Figure 1:
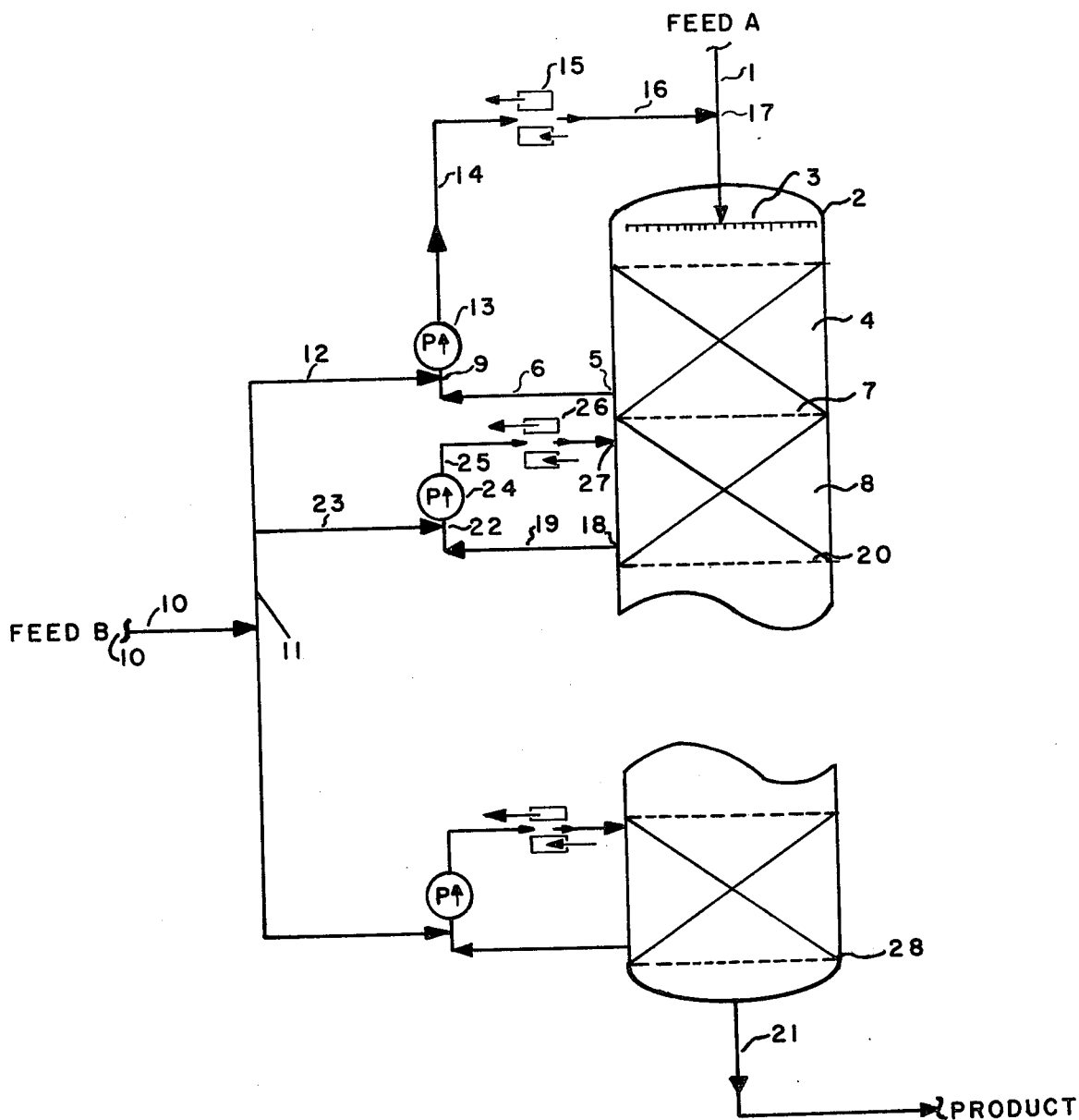

United States Patent [19]

Holmes et al.

[11] 3,976,713

[45] Aug. 24, 1976

[54] ISOPARAFFIN-OLEFIN ALKYLATION UTILIZING RECYCLE STREAMS AND MULTIPLE PACKED CATALYST BEDS

[75] Inventors: Timothy L. Holmes, Pomona, Calif.; Sheldon L. Thompson, Glen Mills, Pa.

[73] Assignee: Sun Oil Company of Pennsylvania, Philadelphia, Pa.

[22] Filed: June 19, 1975

[21] Appl. No.: 588,569

Related U.S. Application Data

[63] Continuation-in-part of Ser. No. 152,167, June 11, 1971, abandoned.

[52] U.S. Cl. .......................................... 260/683.45
[51] Int. Cl.² .......................................... C07C 3/52
[58] Field of Search .................. 260/683.45, 683.43, 260/683.53, 683.64

[56] References Cited
UNITED STATES PATENTS

| | | | |
|---|---|---|---|
| 2,394,368 | 2/1946 | Clarke | 260/683.45 |
| 2,405,097 | 7/1946 | Neuhart | 260/683.45 |
| 2,418,146 | 4/1947 | Upham | 260/683.53 |

*Primary Examiner*—G. J. Crasonakis
*Attorney, Agent, or Firm*—J. Edward Hess; Donald R. Johnson; Paul Lipsitz

[57] ABSTRACT

Isoparaffin-olefin alkylation is provided for contacting fluid with granular solids in a plurality of packed beds in series. Fluid effluent from each bed may be separated into two portions, one of which is recycled to the inlet to that bed and the other of which passes to the inlet of the next bed in the series. Control of the amount and temperature of the recycled fluid permits obtaining similar advantages to those stirred slurry chemical reactors with simplified equipment and handling.

3 Claims, 1 Drawing Figure

ISOPARAFFIN-OLEFIN ALKYLATION UTILIZING RECYCLE STREAMS AND MULTIPLE PACKED CATALYST BEDS

This is a continuation-in-part of application Ser. No. 152,167, filed June 11, 1971 and now abandoned.

BACKGROUND OF THE INVENTION

The present invention relates to a process for contacting fluids with a solid in a series of two or more packed beds with the capability for recycling the effluent of each bed individually to the inlet of that bed. More specifically, the invention is directed to achieving the advantages of a stirred slurry reactor, well known to those skilled in the art, while overcoming the solids handling problem of that type of reactor by approaching its performance with a fixed-bed recycling system. The invention relates to solid catalyst alkylation processes wherein two fluids (liquids or gases), are contacted with a solid catalyst to effect a desired reaction.

Well known in the prior art are processes which embody using a solid catalyst in a stirred slurry-type reactor either singly or in series. These reactors have several disadvantages, one being the solid handling problems when the catalyst requires regeneration. The present invention relates to a fixed bed reactor system that eliminates most of the solids handling problems but has the same advantages as slurry reactors in series. Fixed bed reactors, however, have their own inherent problems, one of which is uncontrolled heat build-up and "hot-spotting" at one or more points in the system. This can result not only in loss of product yield, but can also quickly destroy catalytic activity. Although fixed-bed reactors are well known in the prior art, a process adapting this type of reactor for individual recycle capability to effect the type of reacting usually done in stirred tank reactors has previously been unexplored.

THE INVENTION

It is, therefore, an object of the present invention to provide a process for contacting fluids in a series of two or more fluid-solid contacting zones and to improve such process with the addition of recycle capabilities around each individual zone so as to approach the advantages achieved in a stirred slurry-type of contacting zone and to reduce heat build-up within the beds. It is also within the scope of this invention to attenuate the recycle streams of the sequential zones so as to achieve a series of stirred type and plug flow type contacting zones by increasing or eliminating recycle so as to simulate the former and latter type of contacting zones.

These and other objectives and the advantages of the present invention will become more readily apparent as the invention is more fully set forth hereinafter.

In the present invention these objectives are achieved by the use of a novel processing method for recycling the effluent of each packed bed, in a series of two or more packed beds, to the inlet portion of that packed bed.

One embodiment of the invention is clearly set forth in the FIGURE where there is illustrated a cut-away elevational view of a typical multi-bed reactor containing a plurality of catalysts beds supported by conventional supports and separated by conventional separation and redistribution apparatus well-known in the prior art, and for the sake of simplicity, not shown in the FIGURE. The novel process flow of this invention is shown schematically and will now be described in detail.

Referring to the FIGURE, feed A is introduced via conduit 1 into the fixed bed system 2 through conventional distribution means 3. This stream, A, flows downward through the first solid bed 4 to the level of point 5 where a portion of the effluent of bed 4 is trapped out by any of the well known separation means such as trap-out trays and withdrawn through conduit 6. The remainder of the effluent of bed 4 is redistributed by conventional apparatus located at the level of point 7 to the next solid bed in series, bed 8. The portion of the effluent of bed 4 which was withdrawn at point 5 through conduit 6 flows to point 9. Feed B which is introduced at point 10 flows through conduits 10, 11 and 12 in that order joining conduit 6 at point 9. Thus a mixing of Feed B and the effluent of bed 4, is pumped by pump 13 into conduit 14 which carries the comingled stream through heat exchanger 15 where the stream is cooled. The outlet stream of heat exchanger 15 flows through conduit 16 where it joins feed A at point 17. The combination of Feed A, Feed B and the effluent of bed 4 which was withdrawn at level 5 then flows into bed 4 as previously described.

The effluent of bed 4 not recycled via conduit 6 flows into and through bed 8, the next bed in series, to level 18 where a portion of the effluent of bed 8 is trapped out by any well known separation means and withdrawn through conduit 19. If more than two beds exist, as shown on FIG. 1 the remaining effluent of bed 8, the second bed in series, passes onto the next bed in series and the process is repeated. If bed 8 is the last bed, the unrecycled effluent flows directly into a product outlet conduit such as conduit 21.

The portion of the effluent of bed 8 which is trapped out at level 18 and withdrawn via conduit 19 flows to point 22. Feed B, introduced via conduit 10, conduit 11 and conduit 23 in that order, meets the effluent of bed 8 at point 22. The comingled stream is pumped by pump 24 into conduit 25 and is transported by conduit 25 to heat exchanger 26 where the mixture is cooled. The effluent of exchanger 26 is then reintroduced to bed 8 at point 27 to complete the recycle. This stage of the process is repeated at each succeeding bed until the desired number of stages is provided. At this point, shown as level 28, the unrecycled effluent is withdrawn through conduit 21 to product storage facilities or other disposition.

It will be understood, as indicated above that the process is particularly useful for alkylation where two liquid reactants are passed through a catalytic bed. Examples of such processes are generally the reaction of an olefin with an isoparaffin to produce a larger isoparaffin. Most importantly, the process will be used to react propene or a butene with isobutane to make highly branched alkylate products for gasoline. However, the process is also of value for catalytic polymerization reactions, as for example, where a $C_3$ or $C_4$ olefin may be used to make low molecular weight polymers and in such system all of the olefin could be introduced as Feed A and then Feed B might be zero.

EXAMPLE A

To illustrate the invention and its advantages more clearly, use of the multi-stage fixed bed reactor for solid alkylation will be described with reference to FIG. 1.

Referring to FIG. 1, *i*-butane, Feed A, is charged to the fixed bed system 2 in about a 6/1 ratio to butene-2, Feed B, which is equally distributed between each of the beds, five beds in this example. A pelleted, 1/16 inch × 1/8 inch rare earth-exchanged type & Linde aluminosilicate catalyst is distributed between the five beds to maintain a weight hourly space velocity of about 2 hour$^{-1}$ in each bed based on feed entering and leaving the bed exclusive of recycle. Recycle/Feed ratios are typically about 10/1 but can be adjusted to obtain the desired product composition. Heat removal, in this example, of about 220 BTU/lb. butene-2 feed at each stage, is required. An operating temperature of about 100°C. is employed. Operating pressure is about 500 psig., and the unit is run liquid full with flow being either upward or downward.

Operation of the above described system yields alkylate product at a level of about 50 weight percent $C_8$ alkylate yield based on butene-2 charged whereas operation of a conventional fixed bed, as is known in the art, with all butene-2 charged to the initial stage yields only about 10 weight percent $C_8$ alkylate yield based on butene-2 charged. Also, catalyst life is only a few hours in duration for the conventional fixed bed unit due to polymer and coke formation, whereas it is as much as several days in the case of the novel system described herein.

After the catalyst is deactivated, regeneration in place is readily accomplished by passing air and combustion gases through the system followed by a steam injection step. In this respect, the invention reactor system is as convenient to regenerate as a conventional fixed bed reactor and has a distinct advantage over a slurry reactor system, which requires removal of the catalyst in order to accomplish regeneration.

The invention claimed is:
1. An alkylation process wherein a catalyst bed of granular solids is contacted with fluid reactants which comprises:
   a. passing a first mixture of an isoparaffin and an olefin fluid through a first bed in a series of at least two packed beds of said granular solids,
   b. separating the fluid effluent from said first bed into a first portion and a second portion,
   c. mixing said first portion with a feed stream of said olefin fluid and passing said second mixture through a heat exchanger to remove heat and then recycling said second mixture through said first bed,
   d. passing said second portion through a second bed in series,
   e. separating the fluid effluent from said second bed into a first portion and a second portion,
   f. mixing said first portion from said second bed with a feed stream of said olefin fluid and passing said third mixture through a heat exchanger to remove heat and then recycling said third mixture through said second bed, and
   g. withdrawing an alkylation product from said second portion of step (e)

2. The process of claim 1 wherein more than two packed beds are employed.

3. The process of claim 1 where alkylation is carried out with an isoparaffin fluid of isobutane and an olefin fluid of butene-2.

* * * * *